(12) United States Patent
Park

(10) Patent No.: US 11,571,448 B2
(45) Date of Patent: Feb. 7, 2023

(54) LACTOBACILLUS RHAMNOSUS LM1019 STRAIN AND COMPOSITION FOR PREVENTING AND TREATING OBESITY OR DIABETES MELLITUS COMPRISING SAME

(71) Applicants: Genome And Company, Gyeonggi-do (KR); Lactomason Co., Ltd., Gyeongsangnam-do (KR)

(72) Inventor: Han Soo Park, Seoul (KR)

(73) Assignees: Genome and Company, Gyeonggi-do (KR); Lactomason Co., Ltd., Gyeongsangnam-do (KR)

( * ) Notice: Subject to any disclaimer, the term of this patent is extended or adjusted under 35 U.S.C. 154(b) by 120 days.

(21) Appl. No.: 16/645,185

(22) PCT Filed: Sep. 6, 2018

(86) PCT No.: PCT/KR2018/010400
§ 371 (c)(1),
(2) Date: Mar. 6, 2020

(87) PCT Pub. No.: WO2019/050287
PCT Pub. Date: Mar. 14, 2019

(65) Prior Publication Data
US 2021/0106630 A1 Apr. 15, 2021

(30) Foreign Application Priority Data
Sep. 6, 2017 (KR) .................. 10-2017-0113645

(51) Int. Cl.
| | |
|---|---|
| *A61K 35/747* | (2015.01) |
| *A61K 35/00* | (2006.01) |
| *A23L 33/135* | (2016.01) |
| *A23K 10/18* | (2016.01) |
| *A23L 33/00* | (2016.01) |
| *A61P 3/04* | (2006.01) |
| *A61P 3/10* | (2006.01) |
| *A61K 9/00* | (2006.01) |
| *C12N 1/20* | (2006.01) |
| *C12R 1/225* | (2006.01) |

(52) U.S. Cl.
CPC ............ *A61K 35/747* (2013.01); *A23K 10/18* (2016.05); *A23L 33/135* (2016.08); *A23L 33/40* (2016.08); *A61K 9/0056* (2013.01); *A61P 3/04* (2018.01); *A61P 3/10* (2018.01); *C12N 1/20* (2013.01); *C12N 1/205* (2021.05); *A23V 2002/00* (2013.01); *A23V 2200/328* (2013.01); *A23V 2200/332* (2013.01); *A23Y 2220/73* (2013.01); *A61K 2035/115* (2013.01); *C12R 2001/225* (2021.05)

(58) Field of Classification Search
None
See application file for complete search history.

(56) References Cited

U.S. PATENT DOCUMENTS

2015/0283186 A1  10/2015  Grompone et al.

FOREIGN PATENT DOCUMENTS

| JP | 2016520305 A | 7/2016 |
|---|---|---|
| KR | 101611837 B1 | 4/2016 |
| KR | 101736033 B1 | 5/2017 |
| KR | 101864347 B1 | 6/2018 |
| WO | 2015172191 A1 | 11/2015 |

OTHER PUBLICATIONS

Kemgang et al. J. Nutr. Biochem. 30: 62-73, 2016.*
Sharma et al. AGE 36: 29686, pp. 1-17, 2014.*
Lee, Hui-Young , et al., "Human originated bacteria, *Lactobacillus rhamnosus* PL60, produce conjugated linoleic acid and show anti-obesity effects in diet-induced obese mice", Elsevier—Biochimica et Biophysica Acta 1761 (2006), May 20, 2006, 736-744.

* cited by examiner

*Primary Examiner* — S. Devi
(74) *Attorney, Agent, or Firm* — Servilla Whitney LLC

(57) ABSTRACT

The present invention relates to a *Lactobacillus rhamnosus* LM1019 strain (accession number KCCM12308P), and a composition for preventing and treating obesity or diabetes mellitus, comprising the same. Specifically, the *Lactobacillus rhamnosus* LM1019 strain of the present invention reduces fat cells, neutral fats, subcutaneous fats, and cholesterol, thus having an effect of preventing and treating obesity, and also reduces the blood glucose concentration and the blood insulin concentration, thereby inhibiting insulin resistance and thus having an effect of preventing and treating diabetes mellitus.

11 Claims, 5 Drawing Sheets
Specification includes a Sequence Listing.

A. Subcutaneous fat   B. Epididymal fat   C. Brown adipose tissue

A. Liver        B. Spleen        C. Kidney hepatocytes with areas of fatty change (arrows)

A. Liver        B. Gonadal fat

LACTOBACILLUS RHAMNOSUS LM1019 STRAIN AND COMPOSITION FOR PREVENTING AND TREATING OBESITY OR DIABETES MELLITUS COMPRISING SAME

CROSS-REFERENCE TO RELATED APPLICATIONS

This application is the National Stage entry PCT/KR2018/010400, filed on Sep. 6, 2018, which claims priority to Korean Application Number 10-2017-0113645 filed Sep. 6, 2017, which are incorporated herein by reference in their entireties.

CROSS-REFERENCE TO SEQUENCE LISTING

The Sequence Listing identified as "00931519.txt" (2,017 bytes), created Sep. 4, 2020, is hereby incorporated by reference.

TECHNICAL FIELD

The present invention relates to a novel *Lactobacillus rhamnosus* LM1019 strain and a composition for preventing and treating obesity or diabetes mellitus, comprising the same. Specifically, the *Lactobacillus rhamnosus* LM1019 strain of the present invention reduces fat cells, neutral fats, subcutaneous fats, and cholesterol, thus having an effect of preventing and treating obesity, and also reduces the blood glucose concentration and the blood insulin concentration, thereby inhibiting insulin resistance and thus having an effect of preventing and treating diabetes mellitus. In addition, the *Lactobacillus rhamnosus* LM1019 is involved in the expression of lipase, a lipolytic enzyme, leptin, an appetite-regulating hormone, and carnitine palmitoyltransferase (CPT), an obesity-related gene.

BACKGROUND ART

Recently, as people's lifestyle, such as dietary life, eating habits or the like, is becoming rapidly westernized due to the increased income level and the industrial development, the number of patients with chronic diseases or adult diseases is rapidly increasing. Obesity is one of the known causes for such diseases.

Obesity is an energy metabolism abnormality caused by the imbalance between energy intake and energy consumption, and is consequently defined as a state of the excess accumulation of neutral fats in the fat cells.

Obesity, on a rising trend, is a chronic and serious disease, with no effective treatment, which is taken as problematic all over the world. Obesity, unlike other diseases, is characterized not only by a physical appearance problem but also by the achievement of related diseases such as metabolic disease, hypertension, diabetes mellitus, hyperlipidemia, arteriosclerosis, ischemic heart disease, fatty liver, gallstone disease and the like along with the body weight gain.

Because obesity is a serious disease in itself and additionally causes a cosmetic problem, efforts have been made to develop a variety of obesity therapeutic agents in various countries around the world and thus several obesity therapeutic agents have been developed. Obesity therapeutic agents which have been developed so far largely belonged to either obesity therapeutic agents of an appetite suppressant class or obesity therapeutic agents of a lipolytic inhibitor class.

Although the obesity therapeutic agents of an appetite suppressant class have advantages such as an excellent efficacy of reducing body weight, the obesity therapeutic agents of an appetite suppressant class have a mechanism of action reducing the food intake amount by acting on the central nervous system, thereby reducing an appetite. However, there are crucial problems that the effect cannot persist for a long period, or serious side effects can be caused if used for a long-term period.

Fenfluramine, sibutramine, and rimonabant have been commercialized as early obesity therapeutic agents of an appetite suppressant class, but the selling thereof was discontinued due to serious side effects of psychiatric disease such as heart disease, the elevation of blood pressure, the increase of heart attack, depression, and suicide.

Orlistat (trade name: Xenical), an obesity therapeutic agent of the lipolytic inhibitor class, acts as an anti-obesity agent by a mechanism of action that irreversibly binds to and inactivates pancreatic lipase, which is a pancreatic lipolytic enzyme that breaks down neutral fats, thereby reducing the absorption of neutral fats and cholesterol, and simultaneously promoting the excretion of neutral fats and cholesterol.

Therefore, if taking orlistat, lipolysis is inhibited, and fats taken as food are not absorbed into the body and excreted, which thereby reduces the amount of fats absorbed into the body, leading to body weight decrease. However, in spite of such an efficacy, orlistat has side effects such as abdominal pain, diarrhea, inhibition of the absorption of fat soluble vitamin and the like, and it is reported that serious liver injury can occur if taking for a long-term period, and thus, the discussion on reconsidering the safety of orlistat is ongoing.

Since most of the currently marketed obesity therapeutic agents have serious side effects, the social demand for obesity therapeutic agents that can effectively treat obesity without side effects is very high. Therefore, various studies have been carried out in the world in order to develop an obesity therapeutic agent which can treat obesity without triggering side effects. However, such an obesity therapeutic agent has not been developed and marketed so far.

On the other hand, a plan of using lactic acid bacteria with an excellent safety as a therapeutic agent is being studied because lactic acid bacteria are not absorbed into the body and exist in symbiotic relationships with the human body while staying in the intestinal space.

Lactic acid bacteria play roles in breaking down fibrous and conjugated proteins into important nutrients while having symbiotic relationships with the digestive system of the human body. As such, probiotics are collectively referred to as living microorganisms that have beneficial influence on the health of a host by ameliorating the intestinal microbial environment of the host in the gastrointestinal tract of an animal (including a human).

Probiotics are recognized as having the ability to regulate metabolism and immunological function. Representative probiotics include a *Lactobacillus* sp. strain, a *Lactococcus* sp. strain and the like. Among them, a *Lactobacillus* sp. strain has been known to play an important role in maintaining a healthy digestive organ and intravaginal environment as a major member of a normal microbial community living in the intestine of the human body.

In this regard, Japanese Patent Application No. 2016520305 (published on Jul. 14, 2016) discloses a WIKIM31 strain of *Lactobacillus sakei* species having an anti-obesity activity, and U.S. Patent Application No. 2015/0283186 (published on Oct. 8, 2015) discloses a *Lactoba-*

*cillus rhamnosus* CNCM I-3690 strain having an effect of managing obesity, and Korean Patent No. 101611837 (published on Apr. 6, 2016) discloses a *Lactobacillus rhamnosus* CBT LR5 strain for preventing or treating obesity and metabolic disease caused by obesity, but both the effect of inhibiting lipolysis and the effect of regulating an appetite in the small intestinal cells or in the digestive tract of these strains have not been disclosed.

Therefore, the present inventors found that, among probiotics, a *Lactobacillus rhamnosus* LM1019 inhibits the mRNA and protein expression of genes involved in inducing the differentiation of 3T3-L1 fat cells, thereby ultimately inhibiting the differentiation of 3T3-L1 fat cells and the accumulation of fats. Based on the above, the present inventors completed the present invention.

DETAILED DESCRIPTION OF THE INVENTION

Technical Problem

The present inventors have studied intensively for the purpose of discovering probiotics having an excellent anti-obesity effect. As a result, the present inventors found that a *Lactobacillus rhamnosus* LM1019 strain has an excellent anti-obesity effect, thereby completing the present invention.

Surprisingly, the LM1019 strain not only achieves effects of inhibiting the differentiation of fat cells, inhibiting the accumulation of fats, and regulating an appetite simultaneously, but also has a remarkable effect of reducing insulin resistance.

The present inventors found that a *Lactobacillus rhamnosus* LM1019 strain exhibits not only an effect of inhibiting the differentiation of fat cells, and inhibiting the accumulation of fats, but also an effect of reducing an appetite and reducing the efficiency of diets simultaneously, thereby being effective in preventing and treating obesity and overweight even during a general diet or a high nutrient diet.

In addition, the present inventors confirmed that a *Lactobacillus rhamnosus* LM1019 strain reduces the blood glucose concentration and the blood insulin concentration, thereby reducing insulin resistance that could occur along with obesity In the present invention, it was confirmed that a *Lactobacillus rhamnosus* LM1019 strain inhibits the differentiation from fat precursor cells into fat cells and the accumulation of fats in the cells, reduces body weight and abdominal fats, and reduces the blood cholesterol level and the like, and through various mechanisms of action, enzymes, hormones, and gene expression, has an effect of treating and preventing not only obesity, but also hyperlipidemia, metabolic disease, and diabetes mellitus.

In addition, the present invention provides a *Lactobacillus rhamnosus* LM1019 strain and a composition for preventing and treating obesity, overweight, hyperlipidemia, metabolic disease, and diabetes mellitus, comprising the same.

Solution to Problem

The present invention relates to a *Lactobacillus rhamnosus* LM1019 deposited with the Korean Culture Center of Microorganisms (KCCM) under accession number KCCM12308P.

The *Lactobacillus rhamnosus* LM1019 of the present invention was deposited with the Korean Culture Center of Microorganisms as KFCC11725P on Aug. 11, 2017 (domestic deposit), and the same strain was deposited with the Korean Culture Center of Microorganisms as KCCM12308P on Sep. 5, 2018 (internationl deposit).

The present invention relates to a *Lactobacillus rhamnosus* LM1019 strain (KCCM12308P) having an efficacy of preventing or treating obesity and diabetes mellitus simultaneously.

The present invention relates to a pharmaceutical composition for preventing or treating obesity or diabetes mellitus, characterized in that the pharmaceutical composition comprises a *Lactobacillus rhamnosus* LM1019 strain, and the *Lactobacillus rhamnosus* LM1019 strain exhibits an effect of suppressing lipolysis in the small intestinal cells or in the digestive tract and an effect of regulating an appetite simultaneously.

In this regard, suppressing lipolysis described above may be achieved by inhibiting an activity of lipase, and regulating an appetite described above may be achieved by reducing the secretion of the hormone leptin.

In addition, in the pharmaceutical composition, the *Lactobacillus rhamnosus* LM1019 strain may reduce insulin resistance.

The present invention relates to a method for treating obesity or diabetes mellitus, comprising administering an effective amount of a *Lactobacillus rhamnosus* LM1019 strain to a subject in need of the treatment of obesity or diabetes mellitus.

In this regard, the *Lactobacillus rhamnosus* LM1019 strain may exhibit an effect of suppressing lipolysis in the small intestinal cells or in the digestive tract of the subject to be administered and an effect of regulating an appetite simultaneously.

In addition, suppressing lipolysis described above may be achieved by inhibiting an activity of lipase, and regulating an appetite described above may be achieved by reducing the secretion of the hormone leptin.

In addition, the *Lactobacillus rhamnosus* LM1019 strain may reduce insulin resistance in the subject to be administered.

The present invention relates to a food composition for preventing or ameliorating obesity or diabetes mellitus, characterized in that the food composition comprises a *Lactobacillus rhamnosus* LM1019 strain (KCCM12308P), and the *Lactobacillus rhamnosus* LM1019 strain exhibits an effect of suppressing lipolysis in the small intestinal cells or in the digestive tract and an effect of regulating an appetite simultaneously, wherein the food composition may be a health functional food, a dairy product, a fermented product, or a food additive.

The present invention relates to an animal feed composition for preventing or ameliorating obesity or diabetes mellitus, characterized in that the animal feed composition comprises a *Lactobacillus rhamnosus* LM1019 strain (KCCM12308P), and the *Lactobacillus rhamnosus* LM1019 strain exhibits an effect of suppressing lipolysis in the small intestinal cells or in the digestive tract and an effect of regulating an appetite simultaneously.

Effect of Invention

The *Lactobacillus rhamnosus* LM1019 strain of the present invention inhibits the differentiation of fat cells and the accumulation of fats in the cells, thereby having an excellent anti-obesity effect.

In addition, the *Lactobacillus rhamnosus* LM1019 strain of the present invention reduces body fat mass, reduces total cholesterol, and reduces neutral fats in plasma and neutral fats in liver tissue, thereby exhibiting an effect of preventing or treating obesity or metabolic disease and hyperlipidemia caused by obesity.

In addition, the *Lactobacillus rhamnosus* LM1019 strain of the present invention reduces the blood glucose concentration and the blood insulin concentration, thereby ameliorating insulin resistance and thus exhibiting an effect of preventing or treating obesity and diabetes mellitus caused by obesity.

In addition, the *Lactobacillus rhamnosus* LM1019 strain of the present invention inhibits the activity of lipase, a lipolytic enzyme, thereby suppressing the absorption of fats into the body and promoting the excretion of fats, and reduces the synthesis of leptin, an appetite-regulating hormone, thereby inhibiting an appetite, and increases the gene expression of carnitine palmitoyltransferase (CPT), an enzyme involved in oxidizing fats and converting them into energy, thereby regulating various enzymes and hormones, and thus having an effect of preventing or treating obesity and a disease caused by obesity.

BEST EMBODIMENT FOR WORKING THE INVENTION

Figure 1:
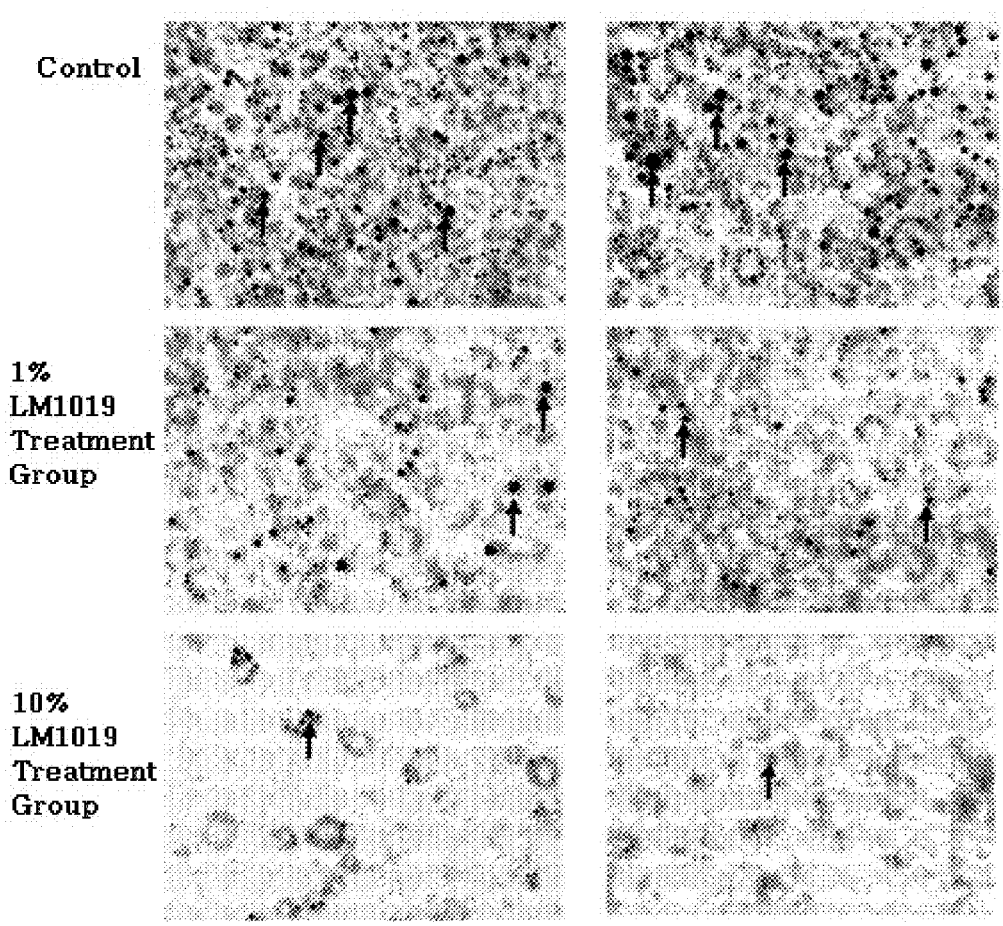
FIG. 1 shows the number of fat globules (arrow) in the fat cells, wherein 3T3-L1 fat precursor cells were treated with 1% and 10% LM1019 culture extracts in 1% and 10% treatment groups respectively and treated with PBS in the control, and the differentiated fat cells were stained with Oil-red-O.

Obesity is a metabolic disorder caused by an imbalance between food intake and energy consumption, and means a state of the excess accumulation of fats in the body. In addition, obesity is closely associated with insulin resistance, glucose tolerance, hyperlipidemia, metabolic disease and the like. Therefore, hyperlipidemia, metabolic disease and diabetes mellitus and the like may occur due to obesity.

Hyperlipidemia is a state in which too many fat substances are present in the blood and build up on the walls of the blood vessels and cause the inflammation, thereby resulting in cardiovascular diseases. Hyperlipidemia may be often caused by the increased level of specific lipids in the blood due to genetic factors, however may also occur due to other causes such as obesity and diabetes mellitus and the like.

Metabolic diseases consist of many metabolic diseases, many of which promote the development of arteriosclerosis and increase the risk of developing cardiovascular diseases. Although the mechanism of action of metabolic diseases is not fully disclosed, most patients suffering from metabolic diseases have an increased concentration of insulin and have insulin resistance.

Diabetes mellitus is a type of metabolic disease that occurs due to abnormal glucose metabolism. Diabetes mellitus is characterized by hyperglycemia in which the blood glucose concentration is elevated, which causes several symptoms and signs, and glucose is excreted into the urine. Although it is known that about 30-70% of diabetes mellitus are determined by genetic influences, a rapid increase in the number of patients with type 2 diabetes mellitus recently in South Korea is closely related to the westernization of lifestyle and the increase in the number of obese patients.

The present invention relates to a composition for preventing or treating obesity or a disease caused by obesity, characterized in that the *Lactobacillus rhamnosus* LM1019 strain exhibits an effect of suppressing lipolysis in the small intestinal cells or in the digestive tract and an effect of regulating an appetite simultaneously.

"Suppressing lipolysis" described above may be achieved by the inhibition of an activity of lipase by the strain, and the reduction of lipolysis in the small intestinal cells or in the digestive tract, thereby the inhibition of the absorption of fats into the body.

Lipase is an enzyme that breaks down neutral fats, which is produced by the pancreas and secreted into the duodenum. Lipase helps the breakdown and absorption of fats. Therefore, when the activity of the enzyme is inhibited, the absorption of fats into the small intestinal cells and into the digestive tract is suppressed along with the breakdown of neutral fats, so that the neutral fats are not absorbed but are excreted into the feces, and consequently the fats accumulated in the body may be reduced. Some bacteria secrete lipase by themselves.

"Regulating an appetite" described above may be achieved by the increase of the secretion of the hormone leptin by the strain, thereby the inhibition or suppression of appetite.

In addition, the present invention relates to a composition for preventing or treating obesity or a disease caused by obesity, characterized in that the *Lactobacillus rhamnosus* LM1019 strain reduces insulin resistance.

Insulin resistance refers to a condition in which cells fail to burn glucose effectively because the function of insulin to reduce the blood glucose level is weakened. Obesity has a direct influence on insulin resistance. As insulin resistance increases, the production of glucose in the liver is not regulated, glucose is not used in the muscle, and the blood glucose is converted to fats in the body, which prevents the accumulation. If insulin resistance is high, the human body produces a large amount of insulin, which can lead to hypertension, hyperlipidemia, diabetes mellitus and the like.

Insulin resistance occurs due to genetic causes and various environmental factors, wherein the environmental factors include lack of exercise, obesity, and excessive calorie intake and the like.

The composition of the present invention may be used in a medicine, a health functional food, a dairy product, a fermented product, a food additive, or an animal feed and the like.

Embodiment for Working the Invention

Hereafter, the present invention will be described in more detail with reference to the following examples. It is intended that these examples illustrate the present invention in more detail and the scope of the present invention is not limited to these examples.

Example 1

Inhibitory Action on Differentiation of Fat Cells and Inhibitory Action on Accumulation of Fats in 3T3-L1 Fat Precursor Cells In order to confirm the inhibitory action on the differentiation of fat cells in fat precursor cells and the inhibitory action on the accumulation of fats in the cells by the *Lactobacillus rhamnosus* LM1019 strain deposited with the Korean Culture Center of Microorganisms (KCCM) under accession number KCCM12308P, the following experiment was carried out.

First, 3T3-L1 fat precursor cells were treated with 1% and 10% LM1019 culture extracts in 1% and 10% treatment groups respectively and treated with PBS in the control, and the differentiated fat cells were stained with Oil-red-O. After one hour, the stained cells were observed with a microscope.

As shown in FIG. 1, the number of fat globules (arrow) in the fat cells was remarkably reduced in the treatment group treated with the LM1019 culture extract as compared with the control treated with PBS instead of the LM1019 culture extract. The same experiment was carried out repeatedly three times.

In particular, it was indicated that, in the case of 10% LM1019 treatment group, the number of fat cells and fat globules was clearly reduced as compared with 1% LM1019 treatment group, and the differentiation of fat cells was clearly different depending on the concentration.

Therefore, it can be seen that the LM1019 culture extract has an effect of inhibiting the differentiation of fat cells and the accumulation of fats in the cells, and the higher the content of the extract, the better the effect is.

Example 2

Promotion of Breakdown of Neutral Fats and Inhibitory Action on Accumulation of Neutral Fats in 3T3-L1 Fat Cells In order to measure the amount of intracellular neutral fats (TGs, triglycerides) accumulated in the process of the differentiation into the fat cells, the 1% and 10% extracts of the LM1019 strain were added respectively, and the cells were cultured. In the control, the cells were cultured by using PBS instead of the extracts of the LM1019 strain. The fat cells on day 9 of the differentiation were harvested and used.

The harvested cells were washed with PBS three times, crushed, and centrifuged at 15,000 rpm at 4° C., and the supernatant was used as a sample. 10 μL of the sample and 150 μL of the enzyme reagent were added, and the reaction was allowed to proceed at ambient temperature for 15 minutes, and the absorbance was measured at 530 nm.

The results of measuring neutral fats in the fat cells are shown in Table 1 below.

TABLE 1

|  | Control | 1% LM1019 treatment group | 10% LM1019 treatment group |
|---|---|---|---|
| Neutral fats (mg/dL) | 42.68 | 38.45 | 15.25 |
| Reduced amount relative to control (%) | 0 | 14.1 | 63.4 |

As shown in Table 1 above, the reduced amounts of neutral fats relative to the control were 14.1% and 63.4% in the 1% LM1019 treatment group and the 10% LM1019 treatment group, respectively.

Therefore, it can be seen that the LM1019 culture extract promotes the breakdown of neutral fats in the fat cells and inhibits the accumulation of fats.

Example 3

Measurement of Lipolytic Enzyme (Lipase) Activity

In order to confirm the lipolytic enzyme (lipase) activity of the LM1019 strain, the following experiment was carried out.

The lipase production medium was prepared, and the LM1019 was streaked with a loop and cultured overnight at 37° C. When lipase was produced, olive oil in the medium was broken down to produce monoglycerides.

The monoglycerides were bound to Rhodamin B in the medium and showed luminescence at 350 nm UV. The experiment was carried out in comparison with the control using *E. coli*, and both of the control and the LM1019 strain group did not show any luminescence.

The concentration of monoglycerides of the control was 0.75 nmol/well and the concentration of monoglycerides of the LM1019 strain group was 0.70 nmol/well. It was confirmed that the concentration of monoglycerides of the strain group was not different from that of the control.

Therefore, it can be seen that the LM1019 strain inhibits the activity of a lipolytic enzyme (lipase), thereby suppressing the absorption of fats into the body and promoting the excretion of fats. In addition, it can be seen that the LM1019 strain does not secrete lipase by itself.

Example 4

Experiment of Anti-Obesity Effect in Laboratory Animals

In order to confirm the anti-obesity effect in mice, 5-week old C57BL6/J mice were tamed for 1 week and then divided into 3 groups, and the following experiment was carried out.

The normal diet (ND, 3.1 kcal/g) in Group 1, the high fat diet (HFD, 5.2 kcal/g) in Group 2, and the high fat diet (HFD) in combination with LM1019 (109 CFU/mouse) in Group 3 were orally administered five times a week, respectively. The body weight and the amount of the administered diet were measured weekly. At week 9, the mice were anatomized, and each of the major organs was extracted and the weight thereof was measured.

Reduction of Body Weight Gain Rate

Figure 2:
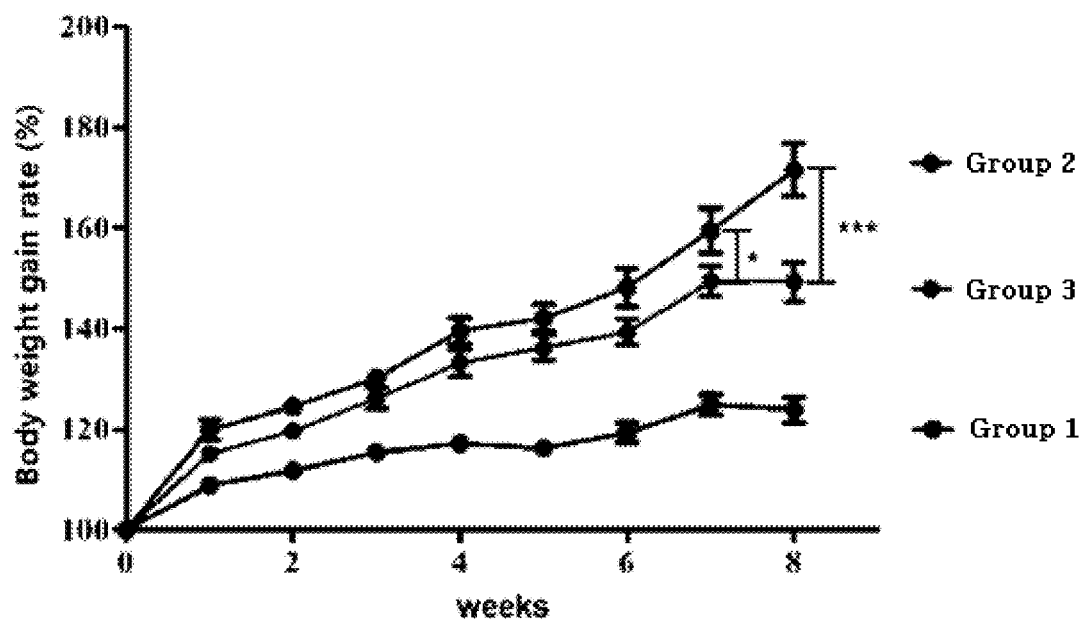
FIG. 2 shows the body weight gain rate depending on time in Group 1 to Group 3.

The body weight at week 0 was regarded as 100%, and the body weight gain rate was measured depending on time and is shown in FIG. 2. As shown in FIG. 2, the body weight gain rate of Group 3 (a group administered with HFD and LM1019) was different from that of Group 2 (HFD) since week 1.

At week 7, the body weight gain rate of Group 3 was 149.43%, and the body weight gain rate of Group 2 was 159.44%. Thus, the body weight gain rate of Group 3 was reduced by 10% in comparison with that of Group 2. At week 8, the body weight gain rate of Group 3 was 149.33%, which was reduced in comparison with that of week 7. In contrast, the body weight gain rate of Group 2 was 171.46%, which was increased by 10% or more in comparison with that of week 7. In particular, at week 8, the body weight gain rate of Group 3 was reduced by 20% or more in comparison with that of Group 2.

As shown in Table 2 below, the amount of body weight gain for 8 weeks of Group 3 was 10.50, and the amount of body weight gain for 8 weeks of Group 2 was 14.84. It was confirmed that the amount of Group 3 is different from that of Group 2 by about 30%.

In the end, as a result of comparing Group 2 administered with the high fat diet and Group 3 administered with the high fat diet in combination with LM1019 at the same time, it can be seen that the difference in the body weight gain rate was shown since week 1, and the difference in the body weight gain rate was remarkably increased over time.

TABLE 2

|  | Group 1 | Group 2 | Group 3 |
| --- | --- | --- | --- |
| Body weight gain rate at week 7 (%) | 124.82 | 159.44 | 149.43 |
| Body weight gain rate at week 8 (%) | 123.92 | 171.46 | 149.33 |
| Amount of body weight gain for 8 weeks (g) | 4.86 | 14.84 | 10.50 |

Reduction of Food Efficiency

The amount of body weight gain for 8 weeks, the weekly food intake amount, the calorie intake amount, and the food efficiency are shown in Table 3 below.

TABLE 3

|  | Group 1 | Group 2 | Group 3 |
| --- | --- | --- | --- |
| Amount of body weight gain (g) | 4.86 | 14.84 | 10.50 |
| Food intake amount (g/mouse per week) | 18.38 | 16.61 | 15.92 |
| Calorie intake amount (kcal/mouse per week) | 56.99 | 87.05 | 83.40 |
| Food efficiency (amount of body weight gain/food intake amount) | 0.03 | 0.11 | 0.08 |

As shown in Table 3 above, it was confirmed that, when the weekly food intake amount and calorie intake amount were compared, the amount of Group 3 was reduced in comparison with that of Group 2. In addition, as a result of calculating the food efficiency from the amount of body weight gain and the food intake amount, the food efficiency of Group 2 was 0.11, but the food efficiency of Group 3 was 0.08. It can be seen that the amount of body weight gain was much lower than the food intake amount.

Reduction of Subcutaneous Fats, Epididymal Fats, and Brown Adipose Tissue

The amounts of subcutaneous fats, epididymal fats, and brown adipose tissue for 8 weeks were measured and are shown in Table 4 below.

TABLE 4

|  | Group 1 | Group 2 | Group 3 |
| --- | --- | --- | --- |
| Subcutaneous fats (g) | 0.35 | 1.296 | 0.694 |
| Epididymal fats (g) | 0.55 | 2.28 | 1.421 |
| Brown adipose tissue (g) | 0.062 | 0.144 | 0.069 |

Figure 3:
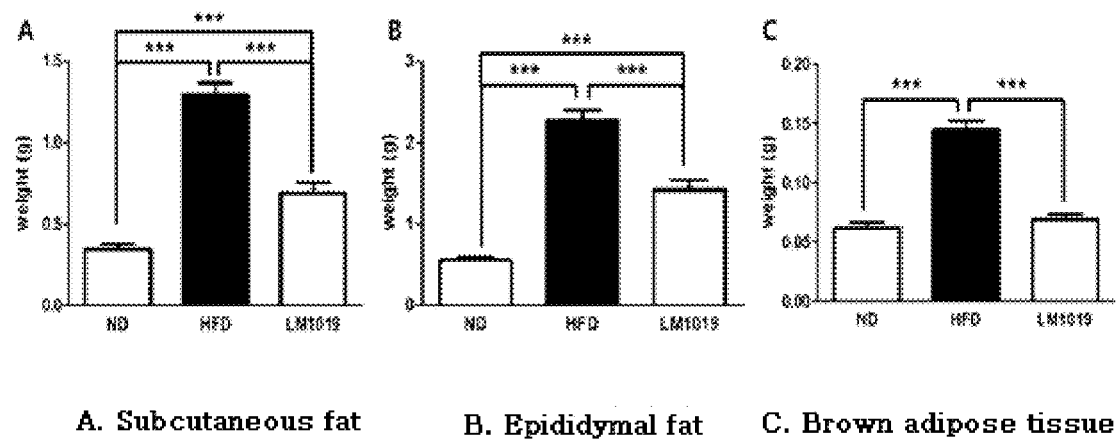
FIG. 3 shows the weights of subcutaneous fats, epididymal fats, and brown adipose tissue in each group.

As shown in Table 4 above and FIG. 3, it was confirmed that the amount of the body fats of Group 3 was remarkably reduced in comparison with that of Group 2.

Figure 4:
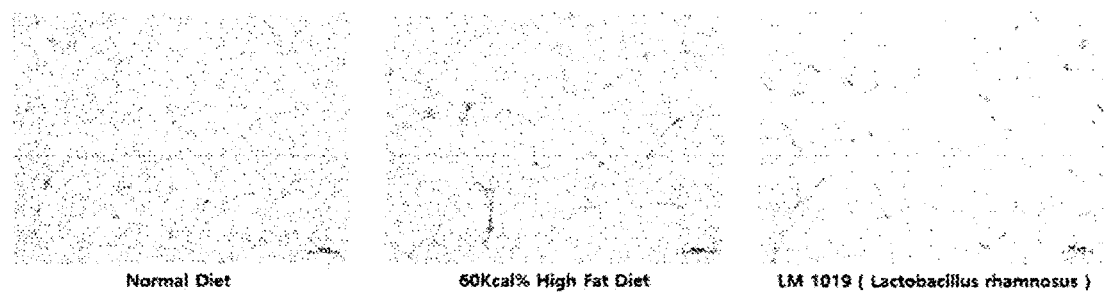
FIG. 4 shows the results of measuring the number of adipose tissue and the size of fat cells stained with H&E stain in epididymal fats in each group.

In addition, the epididymal fats were stained with H&E stain, and the results are shown in FIG. 4. As shown in FIG. 4, it was confirmed that the size of the fat cells of Group 2 was the largest, and the size of the fat cells of Group 3 was reduced to less than half of that of Group 2.

Reduction of Weigtht of Liver

The weights of liver, spleen, and kidney for 8 weeks were measured and are shown in Table 5 below.

TABLE 5

|  | Group 1 | Group 2 | Group 3 |
| --- | --- | --- | --- |
| Weight of liver (g) | 1.12 | 1.508 | 1.053 |
| Weight of spleen (g) | 0.072 | 0.076 | 0.072 |
| Weight of kidney (g) | 0.3 | 0.34 | 0.375 |

As shown in Table 5 above, the weight of liver of Group 3 was remarkably reduced in comparison with that of Group 2. The weights of spleen and kidney did not differ greatly in each group.

Figure 5:
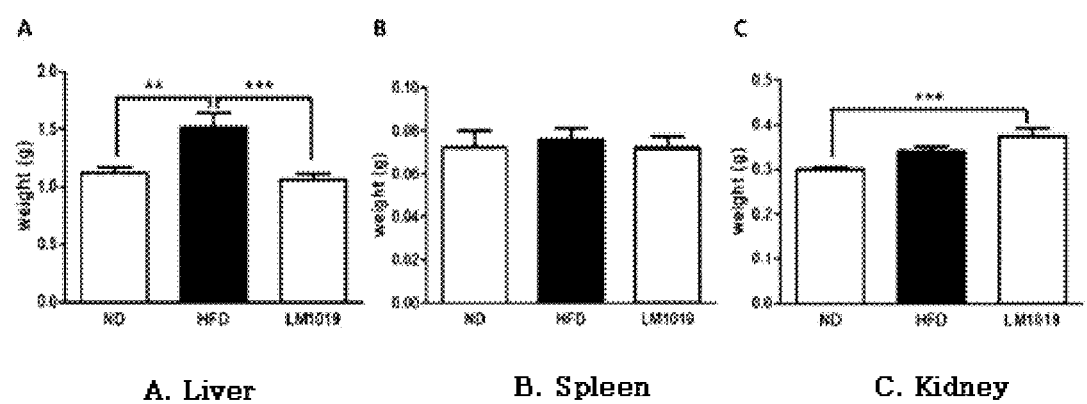
FIG. 5 shows the weights of liver, spleen, and kidney in each group.

In the case of obesity, it is known that fat metabolism in the body occurs abnormally and lipid substances accumulate in the liver, thereby increasing the weight of liver. As shown in Table 5 above and FIG. 5, in the group administered with the LM1019 strain (Group 3), the weight of liver was reduced nearly to a normal level. Thus, it can be seen that the LM1019 strain is involved in lipid metabolism in the liver and has an effect of inhibiting the accumulation of fats in the hepatocytes.

Reduction of Fatty Liver

Figure 6:
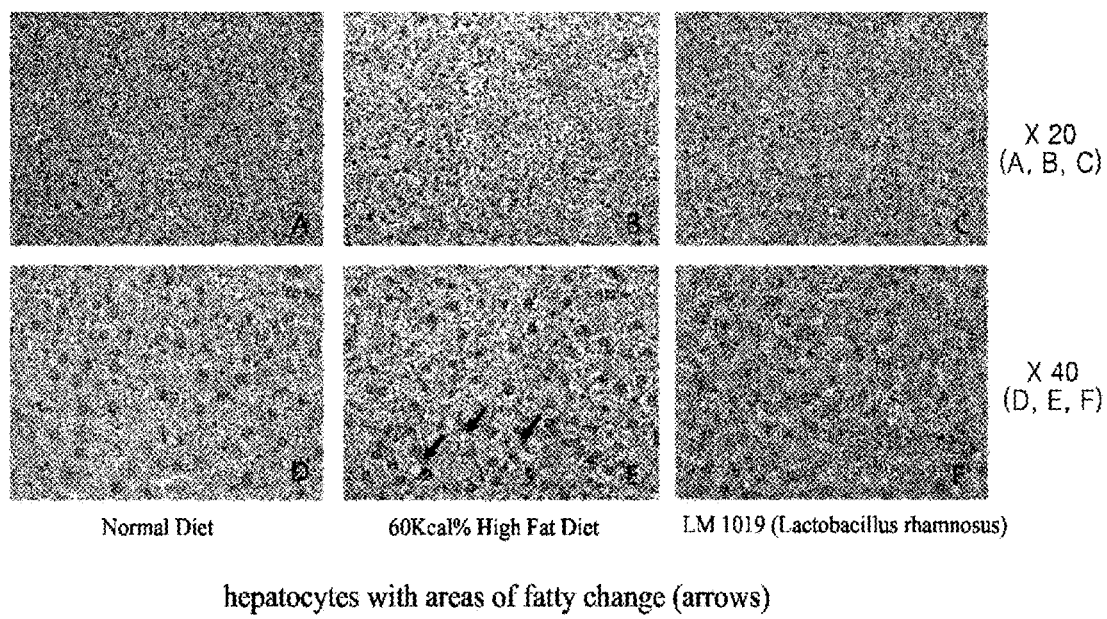
FIG. 6 shows the results of observing the presence or absence of a macro fat vacuole at 20 magnifications (A, B, C) and 40 magnifications (D, E, F) by staining the liver of each group with H&E stain.

The liver was stained with H&E stain, and the presence or absence of a macro fat vacuole (×20 magnifications and ×40 magnifications) was observed and is shown in FIG. 6.

As shown in FIG. 6, macro fat vacuoles were observed all over the liver tissue of Group 2 (red arrow), and no macro fat vacuole was observed in the liver tissues of Group 1 and Group 3.

In the end, it can be seen that the LM1019 strain has an effect of inhibiting fatty liver.

Reduction of Blood Levels of Glucose, Neutral Fats, and Cholesterol The blood levels of glucose, neutral fats, and cholesterol for 8 weeks were measured and are shown in Table 6 below.

TABLE 6

|  | Group 1 | Group 2 | Group 3 |
| --- | --- | --- | --- |
| Glucose (mg/dL) | 228.7 | 320.1 | 230.5 |
| Neutral fats (mg/dL) | 147 | 165 | 103 |
| Cholesterol (mg/dL) | 136 | 218 | 173 |

In the case of obesity, insulin resistance occurs, which leads to the elevated blood insulin levels, resulting in a temporary increase in glucose concentration due to metabolism. As shown in Table 6 above, the blood glucose level of Group 3 was lower than that of Group 2. Thus, it can be seen that the LM1019 strain also has a positive effect on insulin resistance.

In addition, it was confirmed that the blood levels of neutral fats and cholesterol of Group 3 were lower than those of Group 2.

Reduction of Levels of Insulin and Leptin

The levels of insulin and leptin for 8 weeks were measured and are shown in Table 7 below.

TABLE 7

|  | Group 1 | Group 2 | Group 3 |
| --- | --- | --- | --- |
| Insulin (ng/mL) | <0.1 | 1.00 | 0.46 |
| Leptin (ng/mL) | 0.43 | 1.74 | 1.09 |

As mentioned above, in the case of obesity, the insulin resistance is increased, resulting in the increase of the insulin secretion. It was confirmed that the insulin concentration of Group 3 was remarkably reduced as compared with the insulin concentration of Group 2.

Therefore, it can be seen that the LM1019 strain has a remarkable effect of ameliorating insulin resistance through the reduction of blood glucose concentration and blood insulin concentration.

In addition, leptin is an appetite-regulating hormone secreted from fat cells. When neutral fats accumulate in adipose tissue and the size of fat cells increases, the synthesis of leptin is promoted and the concentration of leptin increases.

In the experiment on the concentration of blood neutral fats, the concentration of blood neutral fats of Group 3 was remarkably reduced as compared with that of Group 2. In other words, it can be seen that the concentration of leptin of Group 3 is remarkably reduced as compared with that of Group 2 because neutral fats and fat cells are reduced in Group 2.

Increase of CPT Gene Expression

The liver and epididymal fats of mice that received the LM1019 strain for 8 weeks were extracted, and RNA was extracted using Trizol (Thermo Scientific, USA). Then, DNA complementary to RNA was obtained using Prime-Script™ $1^{st}$ strand cDNA Synthesis kit (TAKARA, Japan), and the expression of CPT2, a gene related to fat oxidation, was analyzed through real-time PCR using SYBR green (TAKARA, Japan).

Carnitine palmitoyltransferase (CPT) gene is an enzyme involved in oxidizing fats and converting them into energy. It can be seen that the higher the level of CPT, the more lipolysis is promoted and the more fats are consumed as energy.

Table 8 below shows the primers used in the experiment, and the mRNA expression of the GAPDH gene is an internal control.

TABLE 8

| No. | Gene | Primer | Sequence | SEQ ID NO |
|---|---|---|---|---|
| 1 | GAPDH | Forward | AGG TCG GTG TGA ACG GAT TTG | 1 |
|   |   | Reverse | TGT AGA CCA TGT AGT TGA GGT CA | 2 |
| 2 | CPT2 | Forward | GCC CAG CTT CCA TCT TTA CT | 3 |
|   |   | Reverse | CAG GAT GTT GTG GTT TAT CCG C | 4 |

Figure 7:
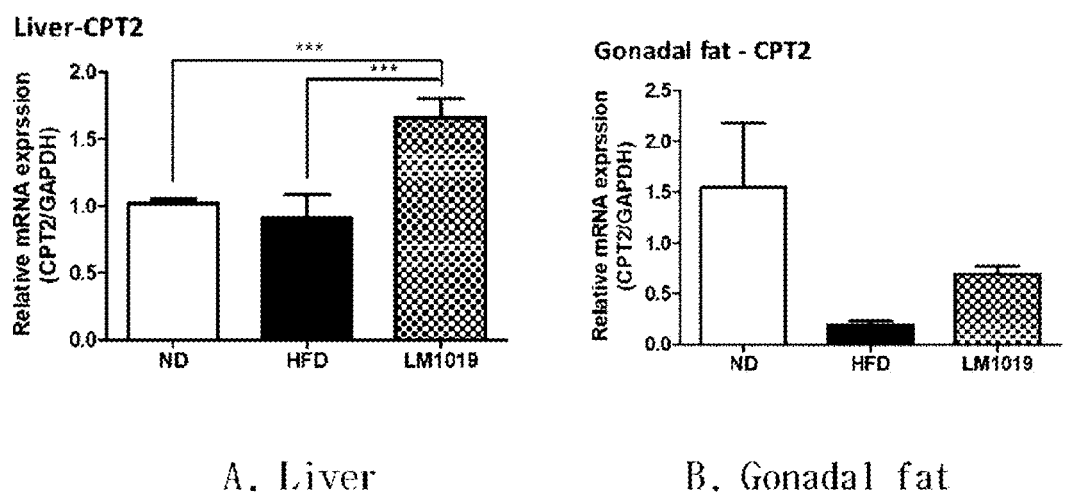
FIG. 7 shows the results of measuring the expression of CPT-2 gene in the liver or epididymal fats of each group.

As shown in FIG. 7, as a result of confirming the expression of CPT-2 gene in the liver and epididymal fats, the expression level of the CPT-2 gene in Group 3, an experimental group, was increased as compared with Group 2. The mean values of 2^-ddCt using GAPDH are shown in Table 9 below.

TABLE 9

|  | Group 1 | Group 2 | Group 3 |
|---|---|---|---|
| CPT2 (liver) | 1 | 0.9081 | 1.66 |
| CPT2 (epididymis) | 1 | 0.188 | 0.6933 |

Therefore, it can be seen that the LM1019 strain has an effect of promoting the expression of an obesity-inhibiting gene.

Reduction of Expression of Obesity-Related Genes in Liver

The expression of SCD1, FAS, and SREBP1, which are obesity-related genes, in the liver was analyzed through real-time PCR using DNA complementary to RNA constructed during the experiment of the expression of CTP gene.

Stearoyl-CoA desaturase-1 (SCD1) is an enzyme that mediates the synthesis of monounsaturated fatty acids. It is highly expressed in obese humans and is closely related to the dysfunction of fat metabolism shown in genetically obese humans or type 2 diabetes mellitus patients.

Fatty-acid Synthase (FAS) is an enzyme that synthesizes fatty acids and is essential for the production of fats in the cells. The increase in the expression thereof can be interpreted as the increase in the synthesis of fats in the cells.

Sterol regulatory element-binding transcription factor 1 (SREBP1) is a binding protein enzyme that regulates the synthesis of fats. This gene is also a gene that has an influence on the synthesis of fats, along with the two genes described above. It can be seen that the higher the level thereof, the more body fats are accumulated.

Table 10 below shows the primers used in the experiment, and the mRNA expression of the 36B4 gene is an internal control.

TABLE 10

| No. | Gene | Primer | Sequence | SEQ ID NO |
|---|---|---|---|---|
| 1 | 36B4 | Forward | CGT CCT CGT TGG AGT GAC A | 5 |
|   |   | Reverse | CGG TGC GTC AGG GAT TG | 6 |
| 2 | SCD1 | Forward | TGG GTT GGC TGC TTG TG | 7 |
|   |   | Reverse | GCG TGG GCA GGA TGA AG | 8 |
| 3 | FAS | Forward | GCC CAG CTT CCA TCT TTA CT | 9 |
|   |   | Reverse | CAG GAT GTT GTG GTT TAT CCG C | 10 |
| 4 | SREBP1 | Forward | TAG TCC GAA GCC GGG TGG GCG CCG GCG CCA T | 11 |
|   |   | Reverse | GAT GTC GTT CAA AAC CGC TGT GTG TCC AGT TC | 12 |

Figure 8:
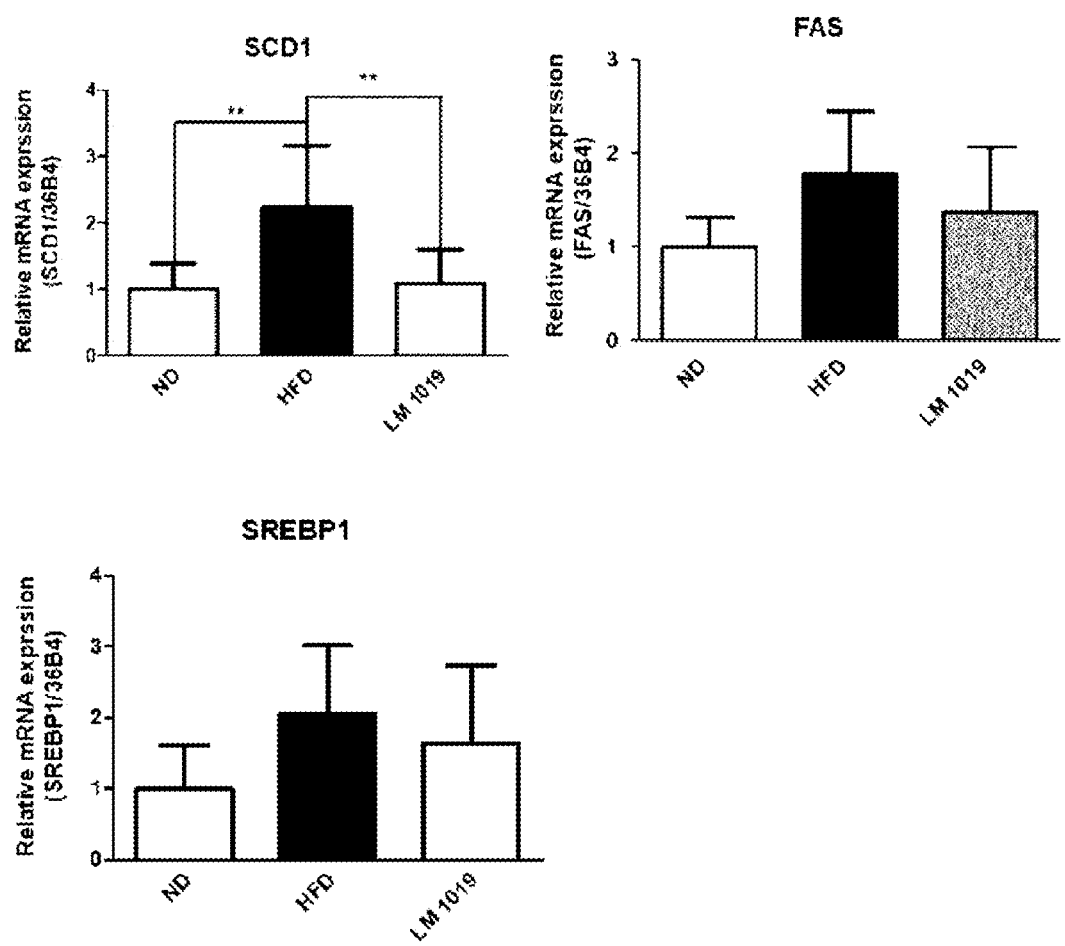

As shown in FIG. 8, as a result of confirming the expression of SCD1, FAS, and SREBP1 genes in the liver, the expression levels of the genes in Group 3, an experimental group, were reduced as compared with Group 2. The mean values of 2^-ddCt using 36B4 are shown in Table 11 below.

TABLE 11

|  | Group 1 | Group 2 | Group 3 |
|---|---|---|---|
| SCD1 | 1 | 2.238 | 1.098 |
| FAS | 1 | 1.779 | 1.366 |
| SREBP1 | 1 | 2.052 | 1.643 |

Therefore, it can be confirmed that the LM1019 strain has an effect of inhibiting the expression of the genes involved in the synthesis of fats.

BUDAPEST TREATY ON THE INTERNATIONAL RECOGNITION OF THE DEPOSIT
OF MICROORGANISMS FOR THE PURPOSES OF PATENT PROCEDURE

INTERNATIONAL FORM

| | |
|---|---|
| To. LACTOMASON Co., Ltd.<br>13-10, worasan-ro 950beon-gil,<br>Munsan-eup, Jinju-si,<br>Gyeongsangnam-do, 52840,<br>Republic of Korea | RECEIPT IN THE CASE OF AN ORIGINAL DEPOSIT<br>issued pursuant to Rule 7.1 by the<br>INTERNATIONAL DEPOSITARY AUTHORITY<br>identified at the bottom of this page |

I. IDENTIFICATION OF THE MICROORGANISM

| | |
|---|---|
| Identification reference given by the DEPOSITOR:<br>*Lactobacillus rhamnosus* LM1019 | Accession number given by the INTERNATIONAL DEPOSITARY AUTHORITY:<br>KCCM12308P |

II. SCIENTIFIC DESCRIPTION AND/OR PROPOSED TAXONOMIC DESIGNATION

The microorganism identified under I above was accompanied by:
☐ a scientific description
☐ a proposed taxonomic designation
(Mark with a cross where applicable)

III. RECEIPT AND ACCEPTANCE

This International Depositary Authority accepts the microorganism identified under I above, which was received by it on Aug. 11, 2017 (date of the original deposit).[1] (KFCC11725P)

IV. RECEIPT OF REQUEST FOR CONVERSION

The microorganism identified under I above was received by this International Depositary Authority on Aug. 11, 2017 (date of the original deposit) and a request to convert the original deposit to a deposit under the Budapest Treaty was received by it on Sep. 5, 2018 (date of receipt of request for conversion).

V. INTERNATIONAL DEPOSITARY AUTHORITY

| | |
|---|---|
| Name: Korean Culture Center of Microorganisms<br>Address: Yurim B/D<br>45, Hongjenae 2ga-gil<br>Seodaemun-gu<br>Seoul 03641<br>Republic of Korea | Signature(s) of person(s) having the power to represent the International Depositary Authority or of authorized official(s):<br>Date: Sep. 5, 2018 |

[1] Where Rule 6.4(d) applies, such date is the date on which the status of international depositary authority was acquired.
Form BP/4 (sole page)

---

The invention claimed is:

1. A method of ameliorating insulin resistance by reducing the concentrations of blood glucose and blood insulin comprising oral administration of an effective amount of the *Lactobacillus rhamnosus* LM1019 strain deposited under the accession number KCCM12308P to a subject in need thereof.

2. The method of claim 1, wherein the subject is obese.

3. The method of claim 1, wherein the subject has type 2 diabetes mellitus.

4. The method of claim 1, wherein the subject is obese and has type 2 diabetes mellitus.

5. The method of claim 1, wherein the *Lactobacillus rhamnosus* LM1019 strain has a lipolysis-suppressing effect in the small intestinal cells or in the digestive tract and an appetite-regulating effect simultaneously.

6. The method of claim 5, wherein the lipolysis-suppressing effect is achieved by inhibiting lipase activity.

7. The method of claim 5, wherein the appetite-regulating effect is achieved by reducing the secretion of the hormone leptin.

8. The method of claim 5, wherein the *Lactobacillus rhamnosus* LM1019 strain has an insulin resistance-reducing effect.

9. The method of claim 1, wherein the *Lactobacillus rhamnosus* LM1019 strain is provided in a food composition or in a pharmaceutical composition.

10. The method of claim 9, wherein the food composition is a health functional food, a dairy product, a fermented product, or a food additive.

11. The method of claim 1, wherein the *Lactobacillus rhamnosus* LM1019 strain is provided in an animal feed composition.

* * * * *

SEQUENCE LISTING

<160> NUMBER OF SEQ ID NOS: 12

<210> SEQ ID NO 1
<211> LENGTH: 21
<212> TYPE: DNA
<213> ORGANISM: mice

<400> SEQUENCE: 1
aggtcggtgt gaacggattt g                                         21

<210> SEQ ID NO 2
<211> LENGTH: 23
<212> TYPE: DNA
<213> ORGANISM: mice

<400> SEQUENCE: 2
tgtagaccat gtagttgagg tca                                       23

<210> SEQ ID NO 3
<211> LENGTH: 20
<212> TYPE: DNA
<213> ORGANISM: mice

<400> SEQUENCE: 3
gcccagcttc catctttact                                           20

```
<210> SEQ ID NO 4
<211> LENGTH: 22
<212> TYPE: DNA
<213> ORGANISM: mice

<400> SEQUENCE: 4
caggatgttg tggtttatcc gc                                            22

<210> SEQ ID NO 5
<211> LENGTH: 19
<212> TYPE: DNA
<213> ORGANISM: mice

<400> SEQUENCE: 5
cgtcctcgtt ggagtgaca                                                19

<210> SEQ ID NO 6
<211> LENGTH: 17
<212> TYPE: DNA
<213> ORGANISM: mice

<400> SEQUENCE: 6
cggtgcgtca gggattg                                                  17

<210> SEQ ID NO 7
<211> LENGTH: 17
<212> TYPE: DNA
<213> ORGANISM: mice

<400> SEQUENCE: 7
tgggttggct gcttgtg                                                  17

<210> SEQ ID NO 8
<211> LENGTH: 17
<212> TYPE: DNA
<213> ORGANISM: mice

<400> SEQUENCE: 8
gcgtgggcag gatgaag                                                  17

<210> SEQ ID NO 9
<211> LENGTH: 20
<212> TYPE: DNA
<213> ORGANISM: mice

<400> SEQUENCE: 9
gcccagcttc catctttact                                               20

<210> SEQ ID NO 10
<211> LENGTH: 22
<212> TYPE: DNA
<213> ORGANISM: mice

<400> SEQUENCE: 10
caggatgttg tggtttatcc gc                                            22

<210> SEQ ID NO 11
<211> LENGTH: 31
<212> TYPE: DNA
<213> ORGANISM: mice

<400> SEQUENCE: 11
tagtccgaag ccgggtgggc gccggcgcca t                                  31
```

```
<210> SEQ ID NO 12
<211> LENGTH: 32
<212> TYPE: DNA
<213> ORGANISM: mice

<400> SEQUENCE: 12
gatgtcgttc aaaaccgctg tgtgtccagt tc                            32
```